United States Patent [19]

Scherrer

[11] 4,013,692
[45] Mar. 22, 1977

[54] CERTAIN 3-PHENYL-BENZOFURAN LOWER ALKANOIC ACIDS AND ESTERS THEREOF

[75] Inventor: Robert A. Scherrer, White Bear Lake, Minn.

[73] Assignee: Riker Laboratories, Inc., Northridge, Calif.

[22] Filed: Nov. 28, 1975

[21] Appl. No.: 636,351

Related U.S. Application Data

[60] Continuation of Ser. No. 516,583, Oct. 21, 1974, abandoned, which is a division of Ser. No. 199,318, Nov. 16, 1971, Pat. No. 3,862,134.

[52] U.S. Cl. .................................. 260/346.2 R
[51] Int. Cl.$^2$ .................................. C07D 307/20
[58] Field of Search ..................... 260/346.2 R

[56] References Cited

UNITED STATES PATENTS 3,682,976  8/1972  Kaltenbronn et al. ...... 260/346.2 R

Primary Examiner—Henry R. Jiles
Assistant Examiner—Bernard Dentz
Attorney, Agent, or Firm—Cruzan Alexander; Donald M. Sell; Donald C. Gipple

[57] ABSTRACT

Benzofurans and 2,3-dihydrobenzofurans optionally substituted at the 2 position by halogen or lower alkyl, substituted at the 3 position by optionally substituted phenyl, substituted on the benzo ring by a lower alkanoic acid group or a salt, ester or amide thereof, optionally substituted on the carbon of said lower alkanoic group bonded to the benzo ring, and optionally substituted on the benzo ring, are active anti-inflammatory, anti-pyretic and analgesic agents or are intermediates in the preparation of such agents.

22 Claims, No Drawings

CERTAIN 3-PHENYL-BENZOFURAN LOWER ALKANOIC ACIDS AND ESTERS THEREOF

This is a continuation of application Ser. No. 516,583, filed Oct. 21, 1974 now abandoned, which was a division of application Ser. No. 199,318, filed Nov. 16, 1971 now U.S. Pat. No. 3,862,134, and with which SN 516,583 was copending.

The present invention relates to benzofurans and 2,3-dihydrobenzofurans optionally substituted at the 2 position by halogen or lower alkyl, substituted at the 3 position by optionally substituted phenyl, substituted on the 5,6 or 7 position of the benzo ring by a lower alkanoic acid group or a salt, ester or amide thereof, optionally substituted on the carbon of said lower alkanoic group bonded to the benzo ring, and optionally substituted on the benzo ring.

The compounds of the invention are anti-inflammatory agents, or intermediates for the synthesis thereof. Certain benzofuran derivatives containing both phenyl and acetic acid substituents are known to the art. See various publications by J. N. Chatterjea. However, these compounds contain the alkanoic acid substituent on the heterocyclic furan portion of the compound, not the benzo fragment of the benzofuran moiety. In addition, both the 2 and the 3 positions of the furan ring of the compounds of the prior art are interchangeably substituted by the phenyl and acetic acid substituents. The compounds of the art have no known use. In particular they are not known to be active as pharmaceuticals.

It is an object of the invention to provide compounds which are anti-inflammatory agents.

It is an object of the invention to provide compounds which are anti-pyretic agents.

It is an object of the invention to provide compounds which are analgesic agents.

It is a further object of the invention to provide a method for controlling inflammation in mammalian tissue.

It is a further object of the invention to provide a method for controlling fever.

It is a further object of the invention to provide a method for relieving pain.

It is still another object of the invention to provide anti-inflammatory compositions containing one or more substituted benzofurans and 2,3-dihydrobenzofurans as active ingredients therein.

It is still another object of the invention to provide anti-pyretic compositions containing one or more substituted benzofurans and 2,3-dihydrobenzofurans as active ingredients therein.

It is still another object of the invention to provide analgesic compositions containing one or more substituted benzofurans and 2,3-dihydrobenzofurans as active ingredients therein.

It is still another object of the invention to provide novel intermediates in the preparation of the antiinflammatory, anti-pyretic and analgesic agents of the invention and processes using the novel intermediates to prepare the active agents.

Still another object will be made apparent by the following specification.

DETAILED DESCRIPTION OF THE INVENTION

According to the present invention, there is provided a class of compounds of the formula

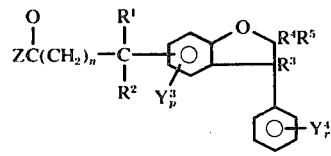

wherein

Z is hydroxyl, lower alkoxy, $-NH_2$, $-NHY^1$, $-NY^1Y^2$,

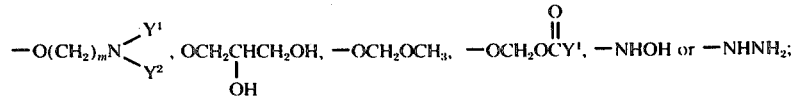

$-NHOH$ or $-NHNH_2$;

$R^1$ is hydrogen or alkyl containing not more than two carbon atoms;

$R^2$ is hydrogen or, with $R^1$, forms $=CH_2$; $R^3$ and $R^4$ are hydrogen or, together, a carbon-carbon bond; $R^5$ is hydrogen or lower alkyl, provided that when $R^3$ and $R^4$ form a bond, $R^5$ may be halogen;

$Y^1$ and $Y^2$ are lower alkyl or, together, form a cyclic group $-(CH_2)_4-$, $-(CH_2)_5-$, $-(CH_2)_2O(CH_2)_2-$ or

$Y^3$ is lower alkyl, lower alkoxy, halogen, nitro, diloweralkylamino or hydroxyl; $Y^4$ is lower alkyl, halogen, lower haloalkyl, lower alkoxy, lower haloalkoxy, nitro, diloweralkylamino, lower alkylthio, lower alkylsulfonyl, lower alkylsulfinyl or hydroxyl;

$m$ is 2–3; $n$ is 0–2; $p$ is 0–2 and $r$ is 0–5.

Preferably the carbon atom carrying $R^1$ and $R^2$ is substituted at the 6 or 7 position of the benzofuran structure.

The invention also includes pharmaceutically acceptable salts of the acid-form compounds (the compounds in which Z is OH). The word lower in the foregoing and elsewhere herein indicated a group containing not more than four carbon atoms.

The acid-form compounds of the invention and pharmaceutically acceptable salts thereof, are useful as intermediates to prepare the acids. In most cases the esters and amides appear to be converted in vivo to the active acid, and thus they provide pharmaceutical activity of themselves. In addition, the esters and amides have different physical properties, for example solubility. Such a variety of physical properties can be useful to maximize the biological availability of the parent acid by varying the absorption, blood transport, and the like, of the pharmaceutical compounds. In addition, as is known, longer chain fatty acids are degraded in vivo to the lower acid having two less carbon atoms. Thus a 7-benzofuranbutyric acid is considered the metabolic equivalent of the corresponding 7-benzofuranacetic acid in most mammalian species. The corresponding 3-hydroxybutyric acid is the intermediate and hence also is equivalent metabolically to the acetic acid (which has two fewer carbon atoms).

Preferably, in the compounds of the invention, $r$ is 0–2. Presently those compounds wherein

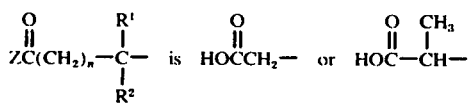

are most preferred.

Additional preferred classes of compounds of the invention are those wherein the phenyl substituent on the furan ring is unsubstituted or halo substituted (especially by fluorine or chlorine, most preferably fluorine); wherein $p$ is zero; and wherein $n$ is zero or one (most preferably wherein n is zero). Preferably also $R^5$ is hydrogen.

In compounds of the invention, wherein $R^2$ is hydrogen and $R^1$ is not hydrogen, the carbon atom to which $R^1$ is chemically bonded is an asymmetric carbon atom. In this case the compounds of the invention are generally present in the form of a racemic mixture. The resolution of such racemates can be carried out by a number of known methods. For example, some racemic mixtures can be precipitated as eutectics instead of mixed crystals and can thus be quickly separated and in such cases can sometimes be selectively precipitated. The more common method of chemical resolution is, however, greatly preferred. By this method diastereomers are formed from the racemic mixture by reaction with an optically active resolving agent. Thus, an optically active base can be reacted with the carboxyl group. The difference in solubility between the diastereomers formed permits the selective crystallization of one form and regeneration of the optically-active acid from the mixture. There is, however, a third method of resolving which shows great promise. This method is one of the other forms of biochemical procedures using selective enzymatic reaction. Thus, the racemic acid can be subjected to an asymmetric oxidase or decarboxylase form, leaving the other form unchanged. Even more attractive is the use of a hydrolysase on a derivative of the racemic mixture to form preferentially one form of the acid. Thus, esters or amides of the acids can be subjected to an esterase which will selectively saponify one enantiomorph and leave the other unchanged.

When the free acid is resolved into (d) and (1) enantiomorphs, the anit-inflammatory activity is found to reside virtually completely in one isomer. For $\alpha$-methyl-3-phenyl-7-benzofuranacetic acid this is the (d) isomer or (+) isomer. The desired isomer of the free acid may be prepared by any one of the preceding described resolving methods, preferably working from the free acid as the starting material. For example, amide or salt diastereomers of the free acid may be formed with optically-active amines, such as quinine, brucine, cinchonidine, cinchonine, hydroxyhydrindamine, menthylamine, morphine, $\alpha$-phenylethylamine, phenyloxynaphthylmethylamine, quinidine, 1-fenchylamine, strychnine, basic amino acids such as lysine, arginine, amino acid esters and the like. Similarly, ester diastereomers of the free acid may be formed with optically-active alcohols, such as borneol, menthol, 2-octanol and the like. Especially preferred is the use of cinchonidine to give the readily decomposable diasteromer salt which may then be resolved by dissolving in a solvent, such as acetone, and distilling the solvent at atmospheric pressure until crystals begin to appear and further crystallization produced by allowing the mixture to cool to room temperature, thereby separating the two enantiomorphs. For example, the (d) acid may then be recovered from the (d) salt by extracting the salt between an inorganic solvent, such as petroleum ether, and dilute hydrochloric acid.

Derivatives of the resolved form of the free acid then may be prepared in the usual way. These derivatives generally are more active than derivatives of racemates of the same compounds. Consequently, the biologically active form of these compounds substantially free of the other form, is a still further aspect of this invention. The active form is generally the (d) form but absolute rotation and even the sign of rotation of the more active form can vary with substitution and compounds must be tested in biological assays to establish their relative activity.

Compounds of the invention wherein $R^1$ and $R^2$ together form a methylene group ($=CH_2$) are all useful as intermediates, but some are also biologically active.

The compounds of the invention are prepared by multistep synthetic sequences. The most convenient of these start with substituted phenols and form substituted benzofuran derivatives. The substituted benzofuran derivatives are then reacted to obtain the aliphatic acid side chain on the benzo ring. Those skilled in the art will recognize that many variations of these sequences exist. The following discussion describes some of the useful processes for obtaining substituted benzofuran derivatives. The temperatures are given in degrees Centigrade. The definitions of the various moieties, such as W, Q, Ar, etc. are uniform unless otherwise noted.

PROCESS A
This process can be represented as follows:

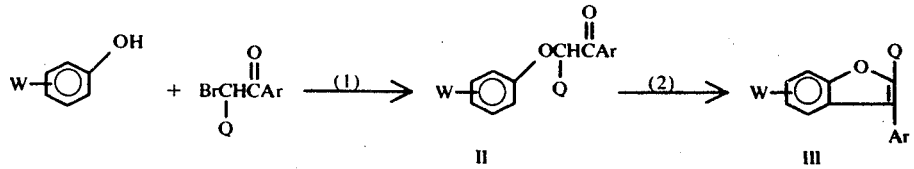

wherein W is bromine, chlorine, iodine or methyl, Q is hydrogen or lower alkyl and Ar is $C_6H_{5-r}$—$Y_r^4$ as in formula I.

The reactants in step (1) are generally known to the art. Equimolar amounts of the reactants, or an excess of the phenol, are reacted in the presence of a base, generally a weak inorganic base such as an alkali metal carbonate. A solvent is used, for example glyme, tetrahydrofuran, ethanol, pyridine and the like and an inert atmosphere may be used. The reaction is carried out at from about 50° to the reflux temperature. The compound of formula II is isolated by conventional methods such as extraction or elution chromatography.

Compounds II wherein W is halogen are known.

In step (2) the compounds of formula II are cyclized by heating in polyphosphoric acid. The known compounds of formula III are easily separated and isolated by dilution of the reaction mixture with water and filtration or extraction.

Rearrangement of Ar from ring position 3 to 2 can occur if care is not taken in the cyclization step when Q = H. The structure of the product is verified by the ultraviolet absorption spectrum. 3-Phenyl derivatives have λ max about 228 and 254, ε about 25,000 and 13,000 respectively, while the 2-phenyl derivatives have λ about 300 with an λ of about 30,000.

PROCESS B

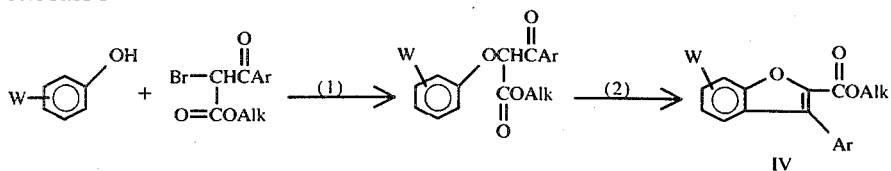

Alk herein is lower alkyl. Steps (1) and (2) are essentially the same as steps (1) and (2) of Process A. The reaction of step (1) uses generally known reactants. The compounds of formula IV are known.

PROCESS C

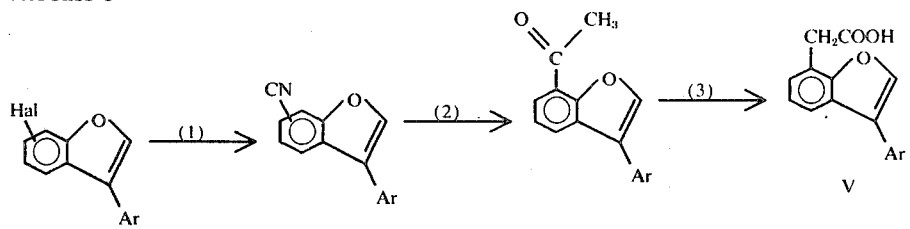

Hal herein is chlorine, bromine or iodine. When this method is used, $R^5$ and $Y^3$ may not be halogen, and Ar is not substituted by halogen. In step (1) the benzofuran is reacted with cuprous cyanide in a solvent such as quinoline. Step (2) is the reaction of the nitrile with methyl Grignard reagent. In step (3) the methyl ketone is converted to a carboxylic acid by, for example, the Willgerodt reaction.

PROCESS D

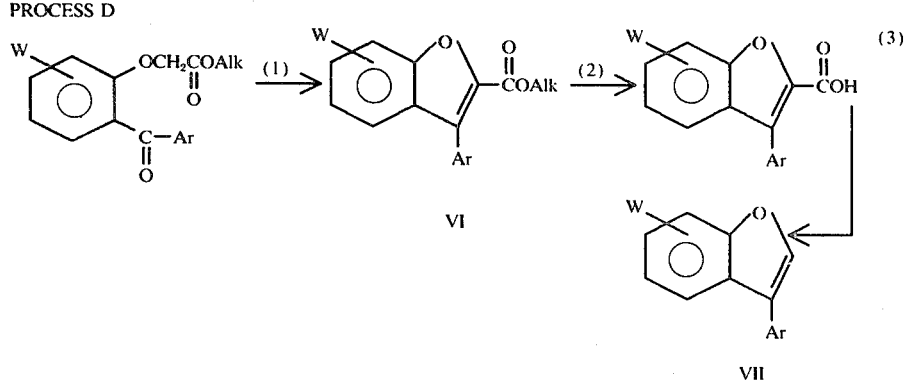

The reactants of step (1) are known cmpounds, readily cyclized in base such as sodium ethoxide in ethanol to the corresponding benzofurans (VI). The compounds of formula VI are isolated by extraction.

In step (2) the hydrolysis of the ester to the acid is carried out under acidic or basic conditions. Alternatively, if W is methyl, hydorlysis is preferably preceded by bromination of the methyl group with N-bromosuccinimide under free-radical conditions such as are known to the art, followed by reaction with an alkali metal cyanide to give cyanomethyl derivative.

Step (3), the decarboxylation, is carried out by any of the well-known methods employed in the art, for example heating in quinoline in the presence of a copper catalyst.

PROCESS E

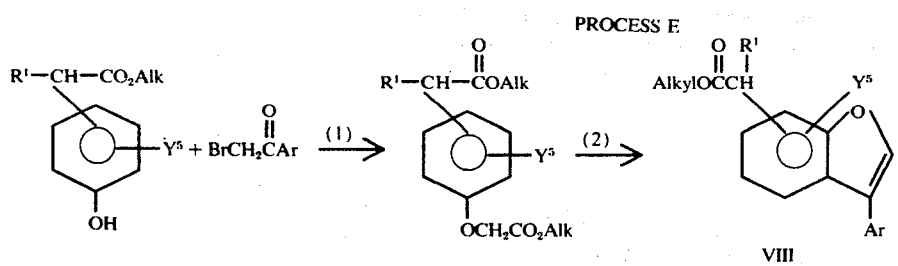

$Y^5$ herein is hydrogen, lower alkyl, lower alkoxy, halogen or dialkylamino. The group $R^1CHCO_2Alk$ cannot be ortho to the hydroxy group in the reactants of this process. In step (1) a phenoxyacetic ester is formed as previously described in Process A, step (1).

In step (2) the cyclizaton is carried out as described in Process A, step (2) to give the novel intermediate VIII. When $Y^5$ is hydrogen, cyclization may occur at either of the positions ortho to the group —OCH$_2$CO$_2$Alk on the benzo ring, and when these positions are non-equivalent, two different isomeric products are formed. These isomers are separated by conventional methods such as elution chromatography, vapor phase chromatography, fractional crystallization, and the like.

The intermediates of formulae III, IV, VI, and VII all contain the benzofuran nucleus with an aryl substituent at the 3 position. These intermediates are then used in further synthetic sequences wherein the objective is to provide compounds which also include the radical $$\underset{R^2}{\overset{\overset{O}{\underset{\|}{\phantom{X}}}\phantom{X}\overset{R^1}{\underset{|}{\phantom{X}}}}{ZC(CH_2)_n-C-}}$$

on the benzo ring as defined hereinabove.

The compounds of formula VIII are compounds of formula I which may be hydrolyzed, under acidic or basic conditions, to provide other compounds of formula I wherein the radical on the benzo ring is

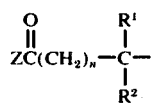

Furthermore, compounds of formula VIII may be transesterified using methods known to the art such as acidic or basic catalysis. The compounds of formula VIII may be converted to carboxylic acid halides by reaction with the usual reagents such as thionyl chloride and phosphorus pentachloride. The acyl halides can then be converted to amides, esters, salts or acids.

The synthetic sequences whereby benzofuran intermediates are converted to compounds of formula I, particularly carboxylic acids, are described further hereinbelow.

PROCESS F

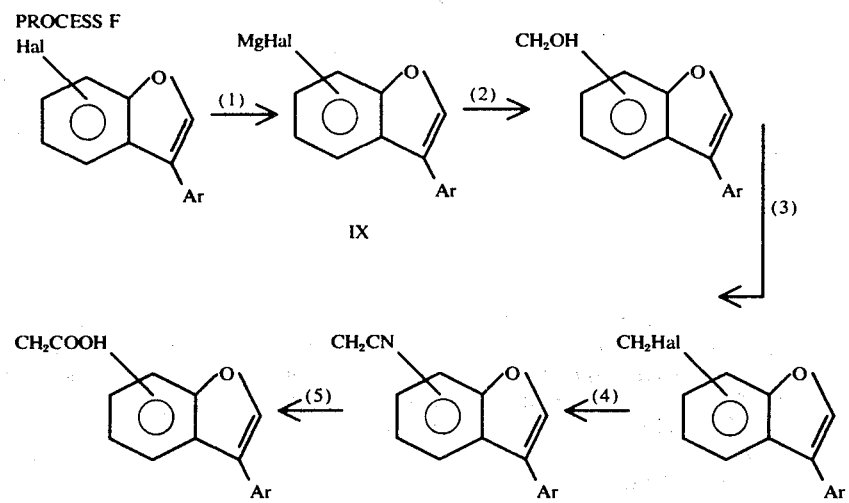

Step (1) may be carried out by any of the well-known methods for preparing Grignard reagents; tetrahydrofuran is a preferred solvent. Step (2) may be carried out by a standard Grignard reaction with formaldehyde, with subsequent acidification to the alcohol. Step (3) requires displacement of the hydroxyl by a halide by any of the well-known methods of the art; for example reaction with a hydrohalogen acid, a phosphorus acid or thionyl halide, or conversion to the mesylate or tosylate. The reaction is preferably carried out in an inert solvent (for example benzene, toluene, xylene and the like) with thionyl chloride at any suitable temperature, but especially in benzene at reflux temperature until the reaction is substantially complete.

The displacement of the halide with a cyanide by any of the well-known methods of the art is the reaction of step (4). Suitable inorganic cyanides, for example sodium cyanide, potassium cyanide and the like, are reacted in an inert solvent, such as dimethylsulfoxide, dimethoxyfuran, acetone, aqueous alcohol and the like. As an example the reaction is carried out in an acetone-ethanol-water mixture with potassium cyanide at any suitable temperature, for example at the reflux temperature of the reaction mixture until the reaction is substantially complete.

an inert solvent such as lower alkanols, aromatic compounds, tetrahydrofuran, acetic acid, dioxane and the like at any suitable temperature, 0° C. to reflux temperature of the system, preferably at room temperature until the reaction is substantially complete.

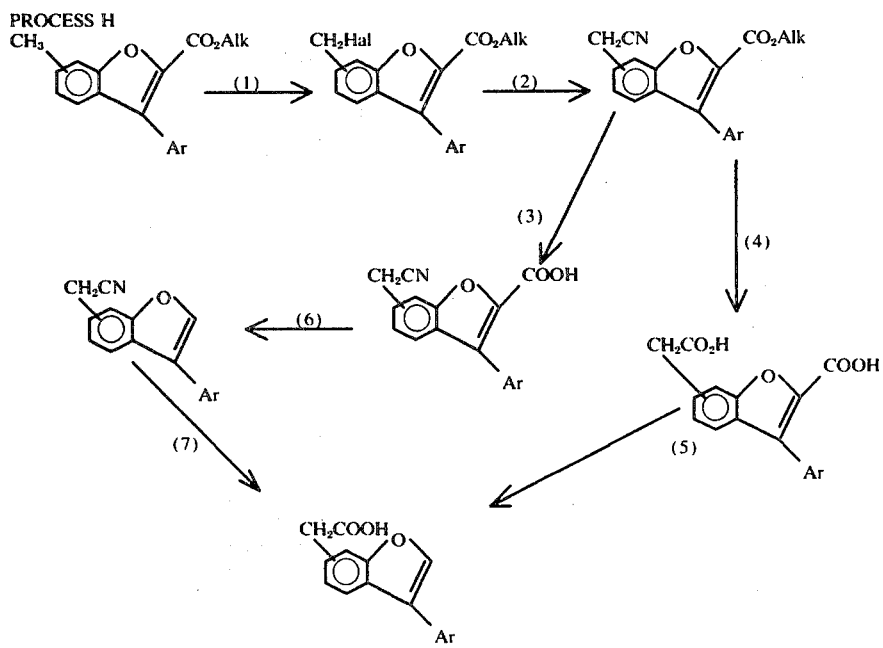

In step (5) the reaction is hydrolysis of the nitrile by any of the variety of the methods well-known to the art, that is acidic, or basic hydrolysis, preferably basic hydrolysis with an alkali metal hydroxide in ethanol.

In step (1) the benzofuran is reacted with a halogenating agent. Presently preferred is N-bromosuccinimide. Free radical conditions which promote side chain halogenation are required, for example cobalt stearate and tertiary-butyl hydroperoxide may be used as a

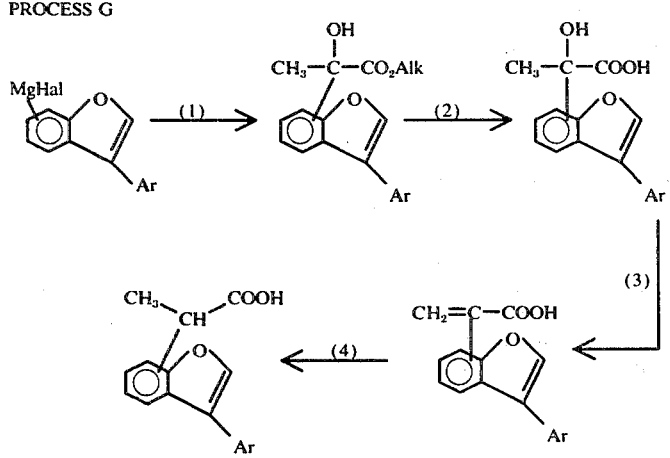

In step (1) the Grignard reagent is reacted with an alpha keto ester, preferably ethyl pyruvate under any of the well-known Grignard condensation type reaction conditions. In step (2) hydrolysis is accomplished by any means well-known to the art. Step (3) is carried out by any dehydration procedure well-known to the art.

Step (4) is catalytic reduction by methods well-known to the art such as reduction over a catalyst, for example palladium, palladium on carbon, platinum, Raney nickel, platinum oxide and the like preferably under moderate hydrogen pressure (5 to 60 pounds) in catalyst combination, and a strong source of visible light is commonly useful.

Step (2), displacement of the halide with a cyanide, is carried out as described in step (4), Process (F).

Step (3), hydrolysis of the ester, is carried by methods well known to the art.

Step (4), simultaneous hydrolysis of the ester and the nitrile is carried out by vigorous hydrolysis with an alkali metal hydroxide in ethanol.

Step (5), selective decarboxylation, is carried out by heating in a quinoline-pyridine mixture until about one mole of carbon dioxide evolved.

Step (6), decarboxylation, is carried out as described in step (3) Process (D).

In step (1) the anionic intermediate is prepared as described in step (1), Process (I). In step (2), the alkylation is carried out as described in step (2), Process (I). The hydrolysis of step (3) is carried out as described in step (5), Process (F).

PROCESS K

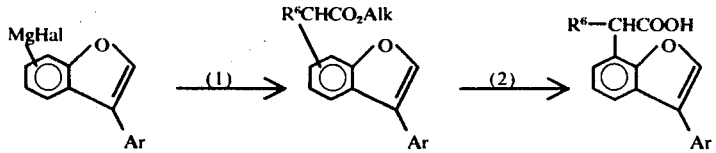

Step (7), hydrolysis of the nitrile, is carried out by the methods described for step (5), Process (F).

Step (1) is a Grignard reaction of a tert butyl alpha-haloacetate, alpha-halopropionate or alpha-halobuty-

PROCESS I

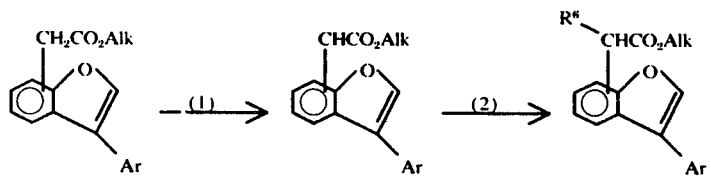

wherein $R^6$ is methyl or ethyl.

In step (1) the benzofuranacetic ester is converted to the reactive anionic intermediate by the action of a strong base such as sodamide, sodium hydride, lithium N,N-dialkylamide and the like. The anionic intermediate is used without isolation for step (2).

In step (2) alkylation is carried out by reaction with an alkyl halide such as methyl bromide, methyl iodide and ethyl bromide in an inert solvent such as benzene, diethyl ether, dimethyl sulfoxide and the like at any suitable temperature from −80° to reflux temperature until the reaction is substantially complete.

rate by methods well known to the art. Step (2) is the hydrolysis of the ester under known acidic or basic conditions.

PROCESS L

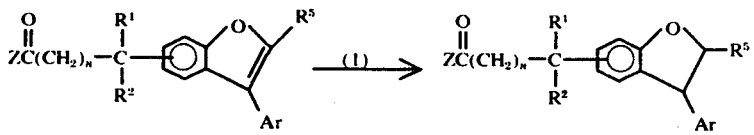

In this process, $R^5$ must be hydrogen or alkyl. The reduction is carried out as in Process G, step (4) but requiring a longer time or more vigorous condition. An example is the use of a catalyst in a lower alkanol such as ethanol as the solvent. The comparable dehydrogenation reaction can also be utilized to form compounds of the invention utilizing known techniques, e.g. heating in decalin in the presence of palladium on charcoal.

PROCESS J

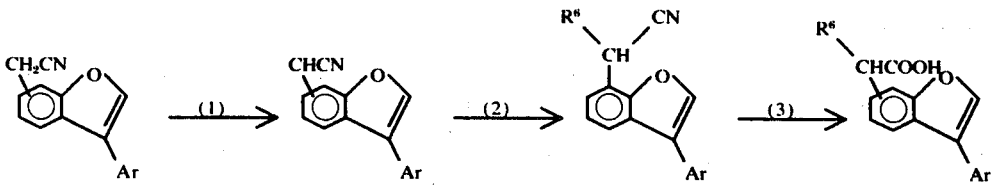

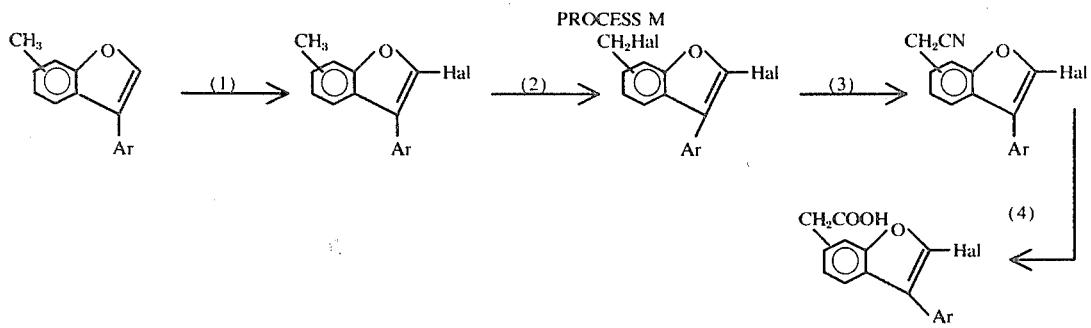

In step (1) the 2 position is halogenated with molecular halogen, preferably in an inert solvent. Chlorine and bromine are the preferred halogens. Step (2) is side-chain halogenation effected as described in step (1), Process H. Step (3) is carried out as described in step (4), Process F. Step (4) is effected using the methods of step (5), Process F, preferably using acidic conditions.

those skilled in the art, for example, the carrageenan or bradykinin induced rat foot edema test, the inhibition of ultraviolet-light-induced erythema test (guinea pig), the rat adjuvant arthritis assay, the Randall-Selitto assay, the phenylquinone writhing assay for analgetic activity and the like. Leading references to the rat foot edema test are:

1. Adamkiewicz et al., Canad. J. Biochem. Physic.

PROCESS N

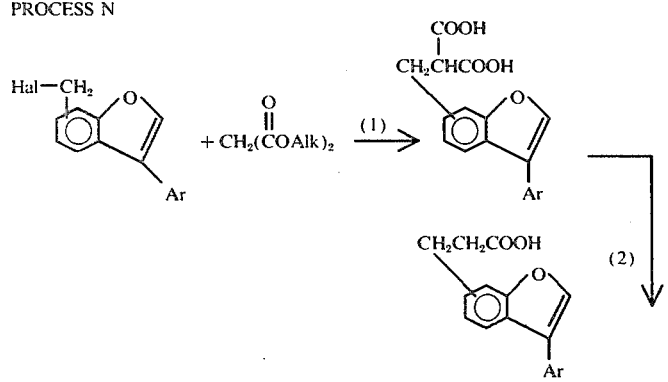

In step (1) the dialkyl malonate is treated with strong base such as sodium hydride, then reacted with the halomethyl-3-arylbenzofuran, preferably in ethanol. In step (2) decarboxylation is readily effected by known methods, for example by heating the dry solid reactant to 150° to 200°.

Compounds of the invention wherein $Y^3$ is not hydrogen are prepared by the processes A through N described hereinabove by incorporating the substituents in the starting phenols, or by appropriate reaction of the intermediates as would be apparent to one skilled in the art. Other transformations of one substituent to another on the structure of formula I, constitute additional processes for the preparations of these compounds. Thus $Y_p^3$ is transformed to another $Y_p^3$ and/or Ar is converted to another Ar and/or $R^5$ to another $R^5$ by methods familiar to those skilled in the art. Examples include reactions as halogenation, nitration, reduction of a nitro group to an amine, alkylation of hydroxy groups and amines and oxidation of sulfides to sulfoxides.

The processes described are illustrative of procedures useful for obtaining the compounds of this invention but are not intended to be limiting. Other processes are known and may be applied by those skilled in the art to obtain the compounds of this invention.

In order to determine and assess the pharmacological activity of the compounds of the invention, testing in animals is carried out using various assays known to 33:332, 1955;
2. Selye, Brit. Med. J. 2:1129, 1949; and
3. Winter, Proc. Soc. Exper. Biol. Med 111:554, 1962.

Leading references to the guinea pig erythema test are:
1. Wilhelmi, Schweiz. Med. Wschr. 79:577; 1949, and
2. Winder et al., Arch. Int. Pharmacodyn. 116:261, 1958.

The compounds of this invention have a high degree of anti-inflammatory activity and are of value in the treatment of arthritic disorders and like conditions which are known to respond to treatment by drugs with anti-inflammatory activity. In addition, the compounds of the invention have a useful degree of antipyretic and analgesic activity. For these purposes they are normally administered orally in tablets or capsules, the optimum dosage depending upon the particular compound being used and the type and severity of the condition being treated. Although the compounds of the invention are preferably administered orally, they may also be administered parenterally or by suppository.

Compounds of the invention are active in one or more of the standard assays. Preferred compounds are active at dosages of 100 mg./kg. or less in one of the assays listed hereinabove, and most preferred compounds have activity equal to or greater than phenylbutazone in one or more of these assays.

The following examples are given for the purpose of further illustrating the procedures of the present invention, but are not intended, in any way, to be limiting on the scope thereof. Thus, while the majority of the examples relate to the acid form compounds (in which Z is OH), the other compounds of the invention can also be prepared. Also, although the examples relate for the most part to compounds in which the furan ring is unsaturated, it is understood that those compounds in which the furan ring is saturated ($R^3$ and $R^4$ are hydrogen) are also contemplated. The melting points are uncorrected, the temperatures are in degrees Centigrade and the pressures in millimeters of mercury.

EXAMPLE 1

Process A, step (1)

Phenacyl bromide (475 g., 2.38 mole) is added to a mixture of 2-bromophenol (400 g., 2.3 mole) and potassium carbonate (470 g., 3.46 mole) in glyme (1600 ml.) under a nitrogen atmosphere and the stirred mixture is heated to reflux temperature and maintained at reflux for 8 hours. Some solid is present. The liquid portion is decanted, then evaporated to dryness. The residue after this evaporation is boiled in benzene and filtered.

The solid pot residue remaining after decanting is extracted with hot benzene several times, and these benzene extracts are combined with the benzene filtrate. Hexane is added to the cooling benzene and a first crop collected. Partial evaporation gives a second crop. The white solid is alpha-(2-bromophenoxy)acetophenone, m.p. 113.5°–115° C.

EXAMPLE 2

Process A, step (2)

Polyphosphoric acid (4200 g.) and alpha-(2-bromophenoxy)acetophenone from Example 1 (596 g., 2.05 mole) are heated and stirred well at about 120° to 125° C. internal temperature for four hours. The reaction mixture is then poured into stirred ice and water (about 8 l. total volume) to give a suspension of white solid. The solid is collected and washed with water, cold dilute sodium hydroxide solution and water until the wash is neutral. The solid is recrystallized from hexane to give white crystals of 7-bromo-3-phenylbenzofuran, m.p. 72°–74° C.

7-methyl-3-phenylbenzofuran is obtained by cyclizing the required acetophenone at about 80° C. for 1 to 2 hours. The optimum temperature and times vary with other substituents which may be present.

Additional novel intermediates of this type prepared by the general method of Process A illustrated by Examples 1 and 2 include:

7-bromo-3-(4-fluorophenyl)benzofuran, m.p. 87°–91° C.
7-bromo-3-(3-chlorophenyl)benzofuran, m.p. 77°–79° C.
7-bromo-3-(4-chlorophenyl)benzofuran, m.p. 116°–117° C.
7-bromo-2-methyl-3-phenylbenzofuran, m.p. 65°–72° C.
7-chloro-3-phenylbenzofuran, m.p. 75.5°–76.5° C.
7-bromo-3-(2-chlorophenyl)benzofuran, m.p. 76°–80° C.
7-bromo-5-methyl-3-phenylbenzofuran, m.p. 48°–50° C.

EXAMPLE 3

Process G, steps (1) and (2)

Dried magnesium turnings (46.2 g., 1.92 mole), dry tetrahydrofuran (200 ml.) methyl iodide (1 ml.) and a small portion of 7-bromo-3-phenylbenzofuran from Example 2 (total 465.7 g., 1.71 mole) are placed in a dry reactor. After the Grignard reaction is observed to be initiated the remaining benzofuran (diluted with 1 liter of tetrahydrofuran is added gradually over 1.5 hours at a rate sufficient to maintain moderate reflux. Heating is continued an additional fifteen minutes, then the mixture is allowed to cool.

Ethyl pyruvate (400 g., 3.45 mole) in dry tetrahydrofuran (3 l.) is cooled to −50° C. and the Grignard mixture is added slowly while maintaining the reaction temperature below −35° C. The mixture is stirred well while allowing it to warm to room temperature over seven hours. The mixture is then heated to its reflux temperature and maintained at reflux for one hour. The mixture is evaporated in vacuo to concentrate it to about 1.5 liters. To this concentrate is added concentrated hydrochloric acid (200 ml.) and 1.5 liters of a mixture of ice and water. The organic phase is separated and the aqueous phase is extracted twice with dichloromethane. The organic phase is combined with these extracts and the solution is washed with saturated sodium chloride solution, then dried and concentrated by evaporation in vacuo to about one liter of an oil which is chiefly ethyl 2-hydroxy-2-[7-(3-phenylbenzofuran)]propionate.

This oil is dissolved in three liters of 95% ethanol and 200 ml. of water and the mixture is heated to its reflux temperature. A solution of potassium hydroxide (232 g.) in water (400 ml.) is added over about one hour. The mixture is maintained at its reflux temperature for 3.5 hours. The mixture is then concentrated to about one-half of its volume and the residue is poured into cold water (1.5 l.). The cloudy mixture is extracted with diethyl ether (700 ml. portions).

The aqueous phase is poured into excess dilute hydrochloric acid and the mixture is cooled and acidified with hydrochloric acid. The solid is collected by filtration and washed with several portions of hot water, then with petroleum ether. The white solid is 2-hydroxy-2-[7-(3-phenylbenzofuran)]propionic acid, m.p. 112.5°–117° C.

Another novel compound of the invention prepared by the general method illustrated by Example 3 is 2-hydroxy-2-{7-[3-(2-methylphenyl)benzofuran]}propionic acid, m.p. 166°–166.5° C. In general the hydroxy acid may be used directly as obtained for the next step.

EXAMPLE 4

Process G, step (3)

Dry 2-hydroxy-2-[7-(3-phenylbenzofuran)]propionic acid (337 g., 1.19 mole) in toluene (3 l.) under a nitrogen atmosphere is treated with para-toluenesulfonic acid hydrate (70 g.) and hydroquinone (1 g.) while refluxing to azeotropically remove water in a Dean-Stark trap. After refluxing for three hours the reaction mixture is cooled, diluted with hexane and cooled by an ice bath. The solid product is collected by filtration washed with petroleum ether, then aqueous ethanol to give 2-[7-(3-phenylbenzofuran)]acrylic acid, m.p. 195.5°–198.5° C.

Additional novel compounds of the invention prepared by the general method illustrated in Example 4 include:

2-[7-(2-methyl-3-phenylbenzofuran)]acrylic acid, m.p. 180°–181° C.

2-{7-[3-(4-chlorophenyl)benzofuran]}acrylic acid, m.p. 175°–181° C.

2-{7-[3-((2-chlorophenyl)benzofuran]}acrylic acid, m.p. 189°–190° C.

2-{7-[3-(3-chlorophenyl)benzofuran]}acrylic acid, an oil

2-{7-[3-(4-fluorophenyl)benzofuran]}acrylic acid, m.p. 204°–206° C.

EXAMPLE 5

Process G, step (4)

2-[7-(3-Phenylbenzofuran)]acrylic acid (40 g., 0.15 mole) is dissolved in warm ethanol (750 ml.) and palladium on charcoal (3 g.) is added. The reduction is carried out using hydrogen gas at 40 psi. initial pressure. The mixture is filtered, then evaporated in vacuo to dryness. The residue is dissolved in benzene (225 ml.) diluted with hexane and cooled. The solid is collected by filtration and again recrystallized from a hexane benzene mixture. The white crystal obtained are 2-[7-(3-phenylbenzofuran)]propionic acid, m.p. 167.5°–168.5° C.

| Analysis: | %C | %H |
|---|---|---|
| Calculated for $C_{17}H_{14}O_3$: | 76.7 | 5.3 |
| Found: | 77.1 | 5.3 |

Additional novel compounds of the invention prepared by the general method illustrated by Example 5 include:

2-[7-(2-methyl-3-phenylbenzofuran)]propionic acid, m.p. 146°–147° C.

2-{7-[3-(4-chlorophenyl)benzofuran]} propionic acid, m.p. 140°–141° C.

2-{7-[3-(3-chlorophenyl)benzofuran]} propionic acid, m.p. 150°–151° C.

2-{7-[3-(4-fluorophenyl)benzofuran]} propionic acid, m.p. 169.5°–171.5° C.

2-{7-[3-(2-chlorophenyl)benzofuran]} propionic acid, m.p. 189°–190.5° C.

EXAMPLE 6

Process F, steps (1) and (2)

Dried magnesium turnings (12.2 g., 0.5 mole), dry tetrahdrofuran (50 ml.), methyl iodide (0.5 ml.) and a small sample of 7-bromo-3-(4-fluorophenyl)benzofuran (total 134 g., 0.46 mole) are placed in a dry reactor. After the Grignard reaction is observed to be initiated an additional 500 ml. of tetrahydrofuran is added, then the remaining benzofuran dissolved in tetrahydrofuran (500 ml.) is added over one hour at a rate sufficient to maintain a gentle reflux. The mixture is heated for an additional hour, then heating is stopped.

Paraformaldehyde (41.4 g., 1.38 mole) (dried over phosphorus pentoxide), is depolymerized at about 160° C. while passing the formaldehyde vapor into and over the stirred Grignard reaction mixture. The reaction is exothermic, causing a gentle reflux. When reaction is complete, the mixture is concentrated to about one-third of its volume, then poured onto ice and water. Diethyl ether (50 ml.) is added, followed by slow addition of concentrated, cold 6N hydrochloric acid (250 ml.). The mixture is extracted with diethyl ether, the extracts are washed with water and saturated sodium chloride solution, dried and evaporated in vacuo to give an oil. The oil is dissolved in absolute ethanol (120 ml.) and concentrated hydrochloric acid (6 ml.) is added. The mixture is heated to reflux temperature and maintained at reflux for 2.5 hours. The mixture is evaporated in vacuo, then the residue is dissolved in diethyl ether, the solution is washed with water and saturated sodium chloride solution, dried and then concentrated to tan oil crude, 3-(4-fluorophenyl)-7-(hydroxymetnyl)benzofuran. Pure product has m.p. 88°–89° C.

An additional novel intermediate compound of the invention prepared by the general method illustrated by Example 6 is:

7-hydroxymethyl-3-phenylbenzofuran, m.p. 76°–77° C. which can be obtained from either 7-bromo-3-phenylbenzofuran or 7-chloro-3-phenylbenzofuran. The crude intermediates can advantageously be used directly in the subsequent steps.

EXAMPLE 7

Process F, step (3)

3-(4-Fluorophenyl)-7-(hydroxymethyl)benzofuran (110 g., 0.45 mole) is dissolved in benzene (225 ml.) and added dropwise to refluxing thionyl chloride (110 ml.). Heating is continued until gas evolution is complete. Excess thionyl chloride and benzene are removed in vacuo, using additional benzene to aid in removing the thionyl chloride. The residue is a brown oil, 7-chloromethyl-3-(4-fluorophenyl)benzofuran.

EXAMPLE 8

Process F, step (4)

To a solution of 7-chloromethyl-3-(4-fluorophenyl)-benzofuran (130.3 g., 0.50 mole) in acetone (750 ml.) and ethanol (500 ml.) is added a solution of sodium cyanide (39.5 g., 0.50 mole) in water 150 ml.). The mixture is heated to its reflux for 5 hours. The mixture is then evaporated in vacuo to concentrate it. The residue is dissolved in dichloromethane, then washed thoroughly with water, dried and concentrated by evaporation in vacuo. The oily residue is recrystallized twice from cyclohexane, then deposited on 70 g. of a magnesium silicate material used for elution chromatography and chromatographed on 400 g. of the silicate type column. Elution with hexane, benzene-hexane (1:4), (1:1) and (3:2), followed by benzene gives the desired product, 7-cyanomethyl-3-(4-fluorophenyl)benzofuran, in the benzene fractions.

Additional novel intermediate compounds of the invention prepared according to the general method illustrated by Example 8 include: 7-cyanomethyl-3-phenylbenzofuran, m.p. 110°–111° C.

7-cyanomethyl-3-(4-chlorophenyl)benzofuran, m.p. 106°–120° C.

EXAMPLE 9

Process F, step (5)

Potassium hydroxide (85%, 49 g.), 7-cyanomethyl-3-(4-fluorophenyl)benzofuran (48.8 g., 0.194 mole) and 95% ethanol (500 ml.) are mixed and heated at reflux temperature overnight under a nitrogen atmosphere. The mixture is then concentrated by evaporation in vacuo, diluted with water and extracted with diethyl ether. The aqueous phase is filtered, then acidified by the slow addition of hydrochloric acid. The solid is collected by filtration and recrystallized from aqueous ethanol (65%) with treatment with decolorizing charcoal, giving yellow crystals. Another recrystallization from an ethanol-petroleum ether mixture (about 5:1)

gives yellow crystals of 3-(4- fluorophenyl)-7-benzofuranacetic acid, m.p. 169°–170° C.

| Analysis: | %C | %H |
|---|---|---|
| Calculated for C₁₆H₁₁FO₃: | 71.1 | 4.1 |
| Found: | 71.0 | 3.8 |

Additional novel compounds of the invention prepared by the general method illustrated by Example 9 include:

3-phenyl-7-benzofuranacetic acid, m.p. 143°–144° C.
3-phenyl-5-benzofuranacetic acid, m.p. 131.5°–132° C.
3-phenyl-7-(5-methoxybenzofuran)acetic acid, m.p. 161°–162° C.
3-phenyl-6-benzofuranacetic acid, m.p. 143°–144° C.
3-phenyl-7-(5-methylbenzofuran)acetic acid, m.p. 134°–135° C.
(2-methyl-3-phenylbenzofuran)-6-acetic acid, m.p. 197°–198° C.
3-(4-methoxyphenyl)-6-benzofuranacetic acid, m.p. 163°–164° C.
3-(4-methylphenyl)-6-benzofuranacetic acid, m.p. 148.5°–156° C.
3-(4-fluorophenyl)-6-benzofuranacetic acid, m.p. 151°–152° C.
3-(4-chlorophenyl)-7-benzofuranacetic acid, m.p. 169°–170.5° C.

The 5 and 6-acetic acids were prepared by way of the esters, Process E.

EXAMPLE 10

Process L

3-Phenyl-7-benzofuranacetic acid (2.5 g., 0.01 mole) is reduced with hydrogen gas using palladium charcoal as catalyst and ethanol as solvent in a Brown hydrogenator. After the absorption of hydrogen stops, the reaction mixture is filtered, then the filtrate is evaporated in vacuo to a white solid. Recrystallization from a benzene-hexane mixture gives white crystals of 2.3-dihydro-3-phenyl-7-benzofuranacetic acid, m.p. 110.5°–111.5° C.

| Analysis: | %C | %H |
|---|---|---|
| Calculated for C₁₆H₁₄O₃: | 75.6 | 5.55 |
| Found: | 75.7 | 5.6 |

EXAMPLE 11

2-[7-(3-Phenylbenzofuran)]propionic acid (2.85 g., 0.107 mole) is dissolved in hot chloroform and added to a solution of cinchonine (1.74 g., 0.0059 mole) in chloroform. The clear solution is then concentrated on a stream bath under a stream of nitrogen. Acetone and a little diethyl ether (total about 40 ml.) are added. The solution is cooled and the precipitate is collected (1.7 g., m.p. 141°–146.5° C.). This precipitate is dissolved in a minimum amount (about 45 ml.) of boiling acetone. The total volume is reduced to 35 ml. and the solution is allowed to stand overnight, then cooled. The solid is collected, 1.44 g., m.p. 148.5°–149° C. Another recrystallization from acetone gives 1.24 g. of white crystals, m.p. 149°–151° C., specific rotation −46° in chloroform. Another recrystallization from acetone gives 1.03 g., m.p. 151.5°–152.5° C., specific rotation −41.5°. The free acid is now obtained by stirring with dilute hydrochloric acid in diethyl ether, 0.50 g., m.p. 158.5°–161° C., specific rotation +58°. After recrystallization from a benzene-n-hexane mixture (6 ml:2 ml), (+)-2-[7-(3-phenylbenzofuran)]propionic acid, 0.40 g., m.p. 157°–162° C.,[α]_D^{23} = +58° (chloroform) is obtained.

| Analysis: | %C | %H |
|---|---|---|
| Calculated for C₁₇H₁₄O₃: | 76.7 | 5.3 |
| Found: | 76.7 | 5.3 |

EXAMPLE 12

Process N

Diethyl malonate (12.7 g., 0.079 mole) is dissolved in ethanol (40 ml.) and treated with sodium hydride (0.079 mole). 7-Chloromethyl-3-phenylbenzofuran (10.0 g., 0.0396 mole) is added and the mixture is heated to its reflux temperature and maintained at reflux for ten hours. Equal volumes of water and diethyl ether are added and the ether extracts are evaporated in vacuo. The residue is dissolved in ethanol and potassium hydroxide (16 g.) is added and the mixture is heated on a steam bath. A yelow solid forms rapidly, but heating is continued overnight. The solution is concentrated by evaporation in vacuo, then equal volumes of water and diethyl ether are added. The ether layer is washed with water, dried, than evaporated to dryness. The residue is recrystallized from benzene to give 3-phenyl-7-benzofuranmethylmalonic acid, m.p. 179°–180° C.

3-Phenyl-7-benzofuranylmethylmalonic acid (1.8 g.) is heated to 180° C. dry, with an oil bath. Gas is evolved for about 10 minutes. The residue is recrystallized from a mixture of benzene-methanol to give 3-[7-(3-phenylbenzofuran)]propionic acid, m.p. 161.5°–162.5° C.

| Analysis: | %C | %H |
|---|---|---|
| Calculated for C₁₃H₁₄O₃: | 76.7 | 5.3 |
| Found: | 76.7 | 5.3 |

EXAMPLE 13

2-{7-[3-(2-chlorophenyl)benzofuran]} propionic acid is dissolved in methanol and treated with an equimolar amount of sodium hydroxide. After stirring at ambient temperature for two hours the reaction mixture is evaporated in vacuo to dryness to give sodium 2-}7-[3-(2-chlorophenyl)benzofuran]} propionate, m.p. 229°–231° C.

| Analysis: | %C | %H |
|---|---|---|
| Calculated for C₁₅H₉ClNaO₂: | 60.0 | 3.7 |
| Found: | 60.2 | 4.1 |

Other salts can be obtained by substituting inorganic or organic bases for the sodium hydroxide, for example calcium hydroxide, aluminum hydroxide, triethylamine and diethanolamine. The choline salt is prepared, e.g. by mixing equivalent weights of a sodium benzofuranacetate and choline chloride in ethanol; it can be isolated by filtering off the sodium chloride formed and either concentrating the solution to dryness or precipitating the salt with acetone or hexane.

EXAMPLE 14

Process M, step (1) and (2)

7-Methyl-3-phenylbenzofuran is treated with an equimolar amount of bromine in carbon tetrachloride at room temperature until decolorized. The mixture is concentrated to dryness to remove hydrobromic acid and redissolved in carbon tetrachloride. To this solution is added an equimolar amount of N-bromosuccinimide and catalytic amounts (about one gram/mole of benzofuran) of cobalt stearate and tertiary-butyl hydroperoxide. The mixture is heated to reflux temperature and maintained at reflux for two hours while shining a bright floodlight directly upon the reaction mixture. The mixture is cooled, filtered to remove succinimide and concentrated in vacuo to a thick oil which slowly crystallizes on cooling to give 2-bromo-7-bromomethyl-3-phenylbenzofuran, m.p. 135°–138° C.

EXAMPLE 15

Process M, steps (3) and (4)

A solution of 2-bromo-7-bromomethyl-3-phenylbenzofuran (35.6 g., 0.092 mole) dissolved in a minimum amount of dimethyl sulfoxide is added to a solution of sodium cyanide (5.9 g., 0.12 mole) in dimethyl sulfoxide (50 ml.) and the mixture is heated at 50° to 60° C. for two hours. The dark solution is then poured over ice and the solid precipitate is collected by filtration. The product is 2-bromo-7-cyanomethyl-3-phenylbenzofuran.

To a mixture of 50% sodium hydroxide solution (35 ml.) and ethanol (100 ml.) is added 2-bromo-7-cyanomethyl-3-phenylbenzofuran (10 g., 0.032 mole). The mixture is heated to reflux temperature and maintained at reflux for about sixteen hours, then concentrated in vacuo. The residue is diluted with water, then extracted (washed) with diethyl ether. The aqueous layer is acidified with hydrochloric acid, yielding a precipitate which is collected by filtration and recrystallized twice from benzene-hexane mixtures to give 2-bromo-3-phenyl-7-benzofuranacetic acid, m.p. 162°–163.5° C.

| Analysis: | %C | %H |
|---|---|---|
| Calculated for $C_{16}H_{11}BrO_3$: | 58.0 | 3.3 |
| Found: | 58.5 | 3.2 |

EXAMPLE 16

Process E, step (3)

Ethyl-3-phenyl-5-benzofuranacetate is prepared by cyclization of α-(4-carbethoxymethylphenoxy)acetophenone in 5 times its weight of polyphosphoric acid at 90° for 30 minutes. Distillation of the crude product gives the desired ester, b.p. ca. 190°/0.01 mm, m.p. 43°–45° C.

Heating 27 g. of ester overnight in 250 ml. of ethanol with 50 ml. of 50% sodium hydroxide gives 3-phenyl-5-benzofuranacetic acid, m.p. 131.5°–132° C. (after recrystallization from aqueous ethanol).

The required aryloxyacetophenone used as starting material is prepared according to the procedure of Example 1.

By the above sequence and starting with methyl p-hydroxyphenyl propionate there is obtained 3-phenyl-5-benzofuranpropionic acid, m.p. 99.5°–100° C.

EXAMPLE 17

A solution of 40 g., of 3-phenyl-7-benzofuranacetic acid in 400 ml. of ethanol and 40 ml. of sulfuric acid is heated under reflux for four hours. The solution is partially concentrated under reduced pressure, poured onto ice and extracted with ether. The ether is washed, dried and concentrated and the residue distilled to give ethyl 3-phenyl-7-benzofuranacetate, b.p. 187°–189°/0.12 mm.

| Analysis: | %C | %H |
|---|---|---|
| Calculated for $C_{18}H_{16}O_3$: | 77.1 | 5.7 |
| Found: | 77.0 | 5.8 |

In a similar manner ethyl 2-[7-(3-phenyl)benzofuranyl]propionate is obtained from the corresponding acid.

Methyl 3-phenyl-7-benzofuranacetate is obtained as above using methanol in place of ethanol or by heating the potassium salt of 3-phenyl-7-benzofuranacetic acid with excess methyl iodide in dimethylformamide at 50°–60° C. for 30 minutes.

EXAMPLE 18

A solution of ethyl 3-phenyl-7-benzofuranacetate, 2.0 g., and hydrazine, 1 g., in 15 ml. of ethanol is heated overnight at reflux. The mixture is cooled and the white precipitate collected. Recrystallation from benzene gives 3-phenyl-7-benzofuranacethydrazide, m.p. 158°–159° C.

| Analysis: | %C | %H | %N |
|---|---|---|---|
| Calculated for $C_{16}H_{14}N_2O_2$: | 72.2 | 5.3 | 10.5 |
| Found: | 72.3 | 5.2 | 10.7 |

EXAMPLE 19

A mixture of 5.0 g. of ethyl 3-phenyl-7-benzofuranacetate, 2.6 g. of hydroxylamine hydrochloride and 6.3 g. of sodium methoxide in 55 ml. of methanol is heated overnight at reflux. Water and dilute hydrochloric acid are added. The precipitate which forms is collected and recrystallized from ethanol to give 3-phenyl-7-benzofuranacethydroxamic acid, m.p. 163° (dec).

| Analysis: | %C | %H | %N |
|---|---|---|---|
| Calculated for $C_{16}H_{13}NO_3$: | 71.9 | 4.9 | 5.2 |
| Found: | 71.6 | 5.1 | 5.2 |

EXAMPLE 20

3-Phenyl-7-benzofuranacetamide is obtained by reaction of the acid chloride (from the acid and thionyl chloride in benzene) with ammonia in ethanol. It has m.p. 163°–164.5° C. when recrystallized from ethanol-water.

EXAMPLE 21

2-Dimethylaminoethyl 2-[7-(3-phenylbenzofuran)]-propionate is obtained by heating 5.0 g. of the propionic acid with 2.7 g. of 2-chloroethyldimethylamine hydrochloride and 3.9 g. of triethylamine in 25 ml. of dimethylformamide for 24 hours. The product is isolated by dilution with 50 ml. of ether, filtration to remove triethylamine hydrochloride, and extraction into 5% hydrochloric acid, from which it is freed with sodium carbonate. The ester is an oil. It can be purified as the hydrochloride, m.p. 186°–187° after recrystallization from isopropanol.

| Analysis: | | %C | %H | %N |
|---|---|---|---|---|
| Calculated for $C_{21}H_{23}NO_3$ HCl: | 67.5 | 6.5 | 3.7 |
| | Found: | 67.6 | 6.6 | 3.8 |

EXAMPLE 22

3Phenyl-7-benzofuranacetic acid, 6.0 g., is heated for 15 minutes with 3.4 g. of sulfuryl chloride in 50 ml. of benzene then left at room temperature overnight to give 2-chloro-3-phenyl-7-benzofuranacetic acid which precipitates from the reaction mixture. Recrystallization from benzene-hexane gives material of m.p. 150.5°–152° C.

| Analysis: | | %C | %H |
|---|---|---|---|
| Calculated for $C_{16}H_{11}ClO_3$: | 67.1 | 3.9 |
| | Found: | 67.3 | 3.8 |

EXAMPLE 23

Starting with 2-bromophenol and alpha-bromo-3,4-dichloroacetophenone and using Process A as described in Examples 1 and 2, the compound 7-bromo-3-(3,4-dichlorophenyl)benzofuran is prepared. Using Process F as described in Examples 6 to 9, this compound is converted to 3-(3,4-dichlorophenyl)-7-benzofuranacetic acid, m.p. 158.5°–160° C.

EXAMPLE 24

A solution of 1.0 g. of 5-methoxy-3-phenyl-7-benzofuranacetic acid in 5 ml. of acetic acid and 1 ml. of 47% hydriodic acid is heated at reflux for 16 hours to obtain the corresponding 5-hydroxy acid. It is isolated by precipitation with water, extraction into ether and then into sodium bicarbonate solution. Recrystallization from benzene gives 5-hydroxy-3-phenyl-7-benzofuranacetic acid, m.p. 197.5°–199° C.

| Analysis: | | %C | %H |
|---|---|---|---|
| Calculated for $C_{16}H_{12}O_4$: | 71.6 | 4.5 |
| | Found: | 71.1 | 4.6 |

EXAMPLE 25

Methyl 2-[7-(3-phenylbenzofuran)]propionate is obtained from methyl 2-[7-(2,3-dihydro-3-phenylbenzofuran)]propionate by heating 20 g. of the latter in 50 ml. of decalin with 5 g. of 5% Pd/C for 24 hours. The ester can be purified by distillation or hydrolyzed as illustrated above to 2-[7-(3-phenylbenzofuran)]propionic acid.

EXAMPLE 26

As an illustration of an acid hydrolysis of nitrile intermediates a mixture of 5 g. of 3-phenyl-7-benzofuranacetonitrile in 30 ml. of acetic acid, 20 ml. of water and 20 ml. of sulfuric acid is stirred and heated at reflux overnight. On cooling and diluting with water one obtains 3-phenyl-7-benzofuranacetic acid, purified by crystallization from benzenehexane.

EXAMPLE 27

Process J, steps (1), (2) and (3)

2-[7-(3-Phenylbenzofuran)]propionic acid is also obtained by a α-methylation. A solution of 2.3 g. of 3-phenyl-7-benzofuran acetonitrile in 15 ml. of glyme is treated with 1.0 equivalents of sodium hydride and the mixture warmed until hydrogen evolution is complete. An excess, 4.0 g., of methyl iodide is added to the cooled mixture and stirred at room temperature overnight. The mixture is concentrated, mixed with 25 ml. of ethanol and 5 g. of 85% KOH and heated at reflux overnight. Work up in the usual manner gives the desired acid.

EXAMPLE 28

2-[7-(3-phenylbenzofuran)]acrylic acid can also be reduced with sodium borohydride to the corresponding propionic acid. Five grams of the acrylic acid methyl ester is stirred at room temperature into 60 ml. of ethanol with 0.68 g. of sodium borohydride for 6 hours. The mix is diluted with water and diluted hydrochloric acid and extracted with ether. The ester is hydrolyzed in ethanol-aqueous sodium hydroxide to obtain 2-[7-(3-phenylbenzofuran)]propionic acid.

EXAMPLE 29

By the procedure illustrated in Examples 1–2 and 6–9 and starting with α-bromo-4-methylthioacetophenone, α-bromo-4-methylsulfinylacetophenone, α-bromo-4-methylsulfonylacetophenone, α-bromo-3-trifluoromethylacetophenone and α-bromo-4-dimethylaminoacetophenone respectively, one obtains:
  3-(4-methylthiophenyl)-7-benzofuranacetic acid
  3-(4-methylsulfinylphenyl)-7-benzofuranacetic acid
  3-(4-methylsulfonylphenyl)-7-benzofuranacetic acid
  3-(3-trifluoromethylphenyl)-7-benzofuranacetic acid
  3-(4-dimethylaminophenyl)-7-benzofuranacetic acid.

EXAMPLE 30

The following amides of the invention are prepared from the acid chloride of Example 20 by reaction with an amine as in Example 20.

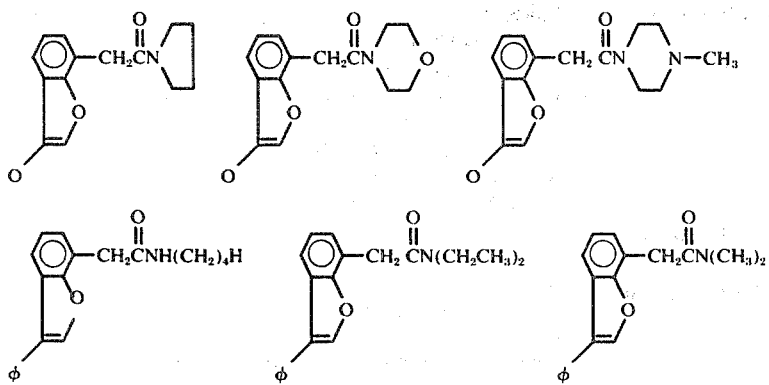

EXAMPLE 31

2-Methyl-4-nitrophenol is converted to 7-methyl-5-nitro-3-phenylbenzofuran by the method of Process A (Examples 1 and 2). This intermediate is brominated with N-bromosuccinimide, providing 2-bromo-7-bromomethyl-5-nitro-3-phenylbenzofuran which is converted by Process F, steps 4 and 5 to 2-bromo-5-nitro-3-phenyl-7-benzofuranacetic acid.

EXAMPLE 32

Using Processes A and F and starting with 2-bromo-4-(N,N-dimethylaminophenol and phenacyl bromide one obtains 5-(N,N-dimethylamino)-3-phenyl-7-benzofuranacetic acid.

EXAMPLE 33

3-(4-methoxyphenyl)-7-benzofuranacetic acid is acetic acid is heated at reflux with 47% hydroiodic acid overnight to provide 3-(4-hydroxyphenyl)-7-benzofuranacetic acid.

EXAMPLE 34

Using the methods of Examples 1 and 2 and 6 to 9 and starting with α-bromo-4-trifluoromethoxyacetophenone one obtains 3-(4-trifluoromethoxyphenyl)-7-benzofuranacetic acid.

EXAMPLE 35

Using Process M as illustrated in Example 14 to 16, 7-methyl-3-(4-nitrophenylbenzofuran (prepared according to Process A) is converted to 2-bromo-3-(4-nitrophenyl)-7-benzofuranacetic acid.

EXAMPLE 36

Using Processes A and F as illustrated in Examples 1 and 2 and 6 to 9 and starting with 2-bromo-4-fluorophenol and phenacyl bromide one obtains 5-fluoro-3-phenyl-7-benzofuranacetic acid.

EXAMPLE 37

The glyceryl ester of 3-phenyl-7-benzofuranacetic acid is prepared by the method described in U.S. Pat. No. 3,478,040, i.e. reacting the acid with chloroacetonitrile in the presence of triethylamine, heating the nitrile with 2,2-dimethyl-1,3-dioxolane-3-methanol in the presence of potassium carbonate and hydrolysis of the isopropylidenedioxypropyl ester.

EXAMPLE 38

The potassium salt of 3-phenyl-7-benzofuranacetic acid is reacted with chloromethoxymethane in dimethylformamide to provide methoxymethyl 3-phenyl-7-benzofuranacetate.

EXAMPLE 39

The potassium salt of 3-phenyl-7-benzofuranacetic acid is reacted with chloromethyl acetate in dimethylformamide to provide acetoxymethyl 3-phenyl-7-benzofuranacetate.

EXAMPLE 40

By the procedures illustrated in Examples 1 and 2 and 6 to 9, and starting with alpha-bromoacetophenone and 2-bromo-4-t-butylphenol one obtains 5-t-butyl-3-phenyl-7-benzofuranacetic acid, m.p. 140.5°–143° C.

What is claimed is:

1. A compound of the formula

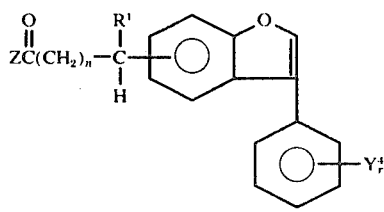

wherein Z is

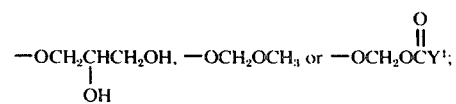

$R^1$ is hydrogen or alkyl containing not more than two carbon atoms, $Y^1$ is alkyl, $Y^4$ is alkyl, halogen, haloalkyl, alkoxy, dialkylamino, alkylthio, alkylsulfonyl, alkylsulfinyl or hydroxyl, each alkyl in $Y^1$ and $Y^4$ containing not more than four carbon atoms; $n$ is 0–2; and $r$ is 0–5; and wherein the group containing Z is attached to the 5,6, or 7 position of the benzofuran ring.

2. A compound according to claim 1 wherein $n$ is 0.
3. A compound according to claim 1 wherein $r$ is 0–2.
4. A compound according to claim 2 wherein $r$ is 0–2.
5. A compound according to claim 1 wherein the carbon atom carrying $R^1$ is substituted at the 6 or 7 position of the benzofuran structure.

6. A compound according to claim 2 wherein r is 0.
7. A compound according to claim 6 wherein $R^1$ is hydrogen.
8. A compound according to claim 1 wherein Z is

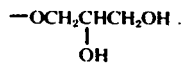

9. The glyceryl ester of 3-phenyl-7-benzofuranacetic acid according to claim 1.
10. Methoxymethyl 3-phenyl-7-benzofuranacetate according to claim 1.
11. Acetoxymethyl 3-phenyl-7-benzofuranacetate according to claim 1.
12. A compound of the formula

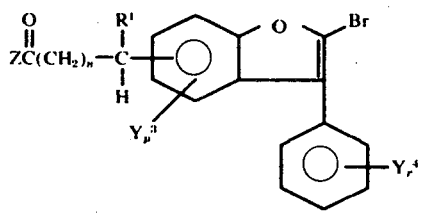

wherein Z is hydroxyl or alkoxy, $R_1$ is hydrogen or alkyl containing not more than two carbon atoms, $Y^3$ is alkyl, alkoxy, halogen, nitro, or hydroxyl; $Y^4$ is alkyl, halogen, haloalkyl, alkoxy, haloalkoxy, nitro, alkylthio, alkylsulfonyl, alkylsulfinyl or hydroxyl, each alkyl in Z, $Y^3$ and/or $Y^4$ containing not more than four carbon atoms; n is 0-2; p is 0-2 and r is 0-5; wherein the group containing Z is attached to the 5,6, or 7 position of the benzofuran ring; and pharmaceutically acceptable salts of the acid-form compounds.

13. A compound according to claim 12 wherein n is 0-1.
14. A compound according to claim 12 wherein p is 0.
15. A compound according to claim 12 wherein r is 0-2.
16. A compound according to claim 13 wherein p is 0.
17. A compound according to claim 13 wherein r is 0-2.
18. A compound according to claim 13 wherein n is 0.
19. A compound according to claim 18 wheren p is 0 and r is 0-2.
20. 2-Bromo-3-phenyl-7-benzofuranacetic acid according to claim 12.
21. 2-Bromo-5-nitro-3-phenyl-7-benzofuranacetic acid according to claim 12.
22. 2-Bromo-3-(4-nitrophenyl)-7-benzofuranacetic acid according to claim 12.

* * * * *